(12) United States Patent
Kuderer et al.

(10) Patent No.: US 6,788,402 B2
(45) Date of Patent: Sep. 7, 2004

(54) METHOD OF REDUCING THE EFFECTS OF VARYING ENVIRONMENTAL CONDITIONS IN A MEASURING INSTRUMENT AND MEASURING INSTRUMENT USING THE METHOD

(75) Inventors: Hubert Kuderer, Waldbronn (DE); Konrad Teitz, Karlsbad (DE); Detlev Hadbawnik, Waldbronn (DE)

(73) Assignee: Agilent Technologies, Inc., Palo Alto, CA (US)

( * ) Notice: Subject to any disclaimer, the term of this patent is extended or adjusted under 35 U.S.C. 154(b) by 302 days.

(21) Appl. No.: 09/880,361

(22) Filed: Jun. 13, 2001

(65) Prior Publication Data

US 2002/0011097 A1 Jan. 31, 2002

(30) Foreign Application Priority Data

Jun. 27, 2000 (EP) .............................................. 00113606

(51) Int. Cl.⁷ .............................................. G01N 21/41
(52) U.S. Cl. ...................................... 356/128; 356/440
(58) Field of Search ........................ 356/246, 432–440, 356/410, 128; 250/238, 352

(56) References Cited

U.S. PATENT DOCUMENTS 4,019,372 A * 4/1977 Parkell et al. ............. 73/61.57
4,348,115 A * 9/1982 Walker et al. .............. 356/436
5,523,563 A 6/1996 Moessner .................... 250/238

FOREIGN PATENT DOCUMENTS

| DE | 43 17 757 | 12/1993 |
| EP | 0 164 080 | 12/1985 |
| GB | 2 068 539 | 8/1991 |
| JP | 61-90056 | * 5/1986 |
| JP | 5094753 U | * 12/1993 |

OTHER PUBLICATIONS

Zinngrebe, U., examiner, European Search Report, Application No. EP 00 11 3606.

* cited by examiner

*Primary Examiner*—Hoa Q. Pham (57) ABSTRACT

A method of reducing the effects of varying environmental conditions on a measuring instrument includes thermally insulating a measuring unit such that the effects of variations of environmental conditions on selected components of the measuring unit are substantially reduced, while allowing dissipated heat generated within the measuring unit to leave the measuring unit. The method also includes controlling a first temperature in the measuring unit by means of a control loop which includes a temperature sensor and means to influence the first temperature in the measuring unit in such a way that temperatures at locations with selected components are kept substantially constant.

14 Claims, 6 Drawing Sheets

METHOD OF REDUCING THE EFFECTS OF VARYING ENVIRONMENTAL CONDITIONS IN A MEASURING INSTRUMENT AND MEASURING INSTRUMENT USING THE METHOD

The invention relates to a method of reducing the effects of varying environmental conditions, such as varying temperature or humidity, on the measuring results in a measuring instrument. The invention also relates to a measuring instrument having reduced effects of varying environmental conditions on the measuring results. The invention can be used with any type of measuring instruments the operation of which is dependent on ambient conditions. A preferred field of use of the invention is in connection with optical instruments, for example optical detectors for liquid chromatography.

BACKGROUND OF THE INVENTION

Varying environmental conditions, such as variations of the ambient temperature or of humidity or of the speed of ambient air, have negative effects on the measuring results in a measuring instrument. In optical instruments, for example, temperature variations impair the measuring results in the following ways:

Thermal expansion of materials changes the dimensions of the optical components and may thus change the optical properties of the instrument Furthermore, mechanical stress is induced by thermal expansion which has an impact on optical image properties.

The emission characteristics of the light source of the instrument is temperature dependent.

The refractive index of a sample to be measured or of a solvent changes with temperature and influences the optical image properties.

The dark current and the sensitivity of a photo sensor used in the instrument is temperature dependent The operation of the electronic circuitry used in the instrument for control and data analysis is also influenced by temperature.

Figure 1:
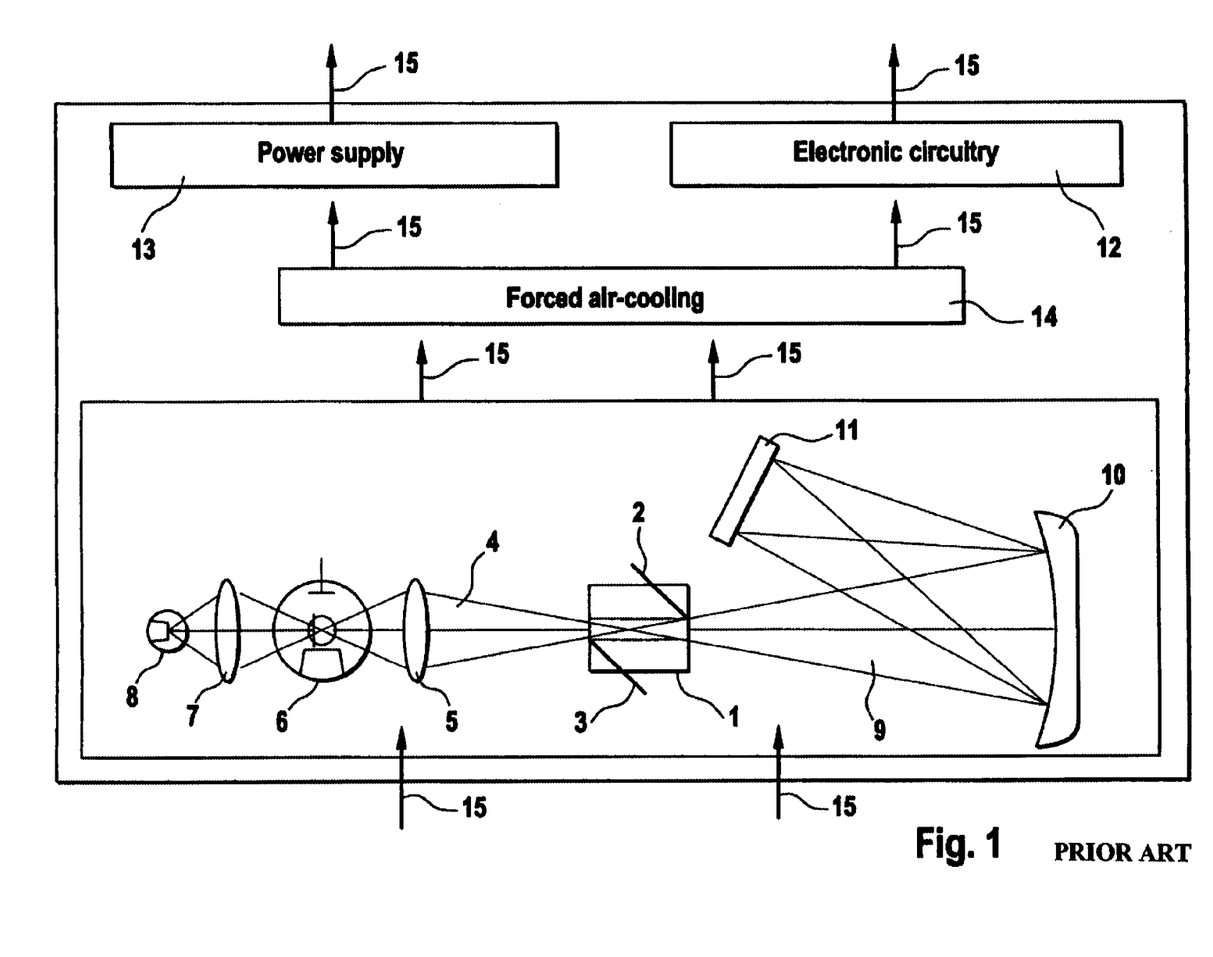
FIG. 1 is a block diagram of a prior art detector for a liquid chromatograph for illustrating the underlying problem of the invention.

In order to further illustrate the underlying problem of the present invention, reference is made to FIG. 1 which is a block diagram of an absorbance detector for a liquid chromatograph. The detector comprises a flow cell 1 with an inlet 3 and an outlet 2 for sample liquid eluting from a chromatographic separation column (not shown). The flow cell 1 is irradiated with a polychromatic light beam 4 generated by a tungsten lamp 8 and a deuterium lamp 6 and shaped by lenses 5 and 7. The light beam 4 entering the flow cell 1 is absorbed by the sample in the cell at specific wavelengths which are characteristic for the sample. The beam 9 leaving the flow cell 1 impinges on a diffraction grating 10 which spatially separates the beam 9 into rays of different wavelengths. The grating 10 directs the rays of different wavelengths onto a sensor 11, typically a photodiode array, where the rays of different wavelengths are detected. The absorbance detector shown in FIG. 1 further comprises electronic circuitry 12, e.g. for controlling the instrument and for data processing and evaluation, and a power supply 13.

The thermal balance and the distortion of the thermal equilibrium in the detector shown in FIG. 1 is determined by several factors, such as:

environmental conditions, mainly ambient temperature;
power dissipation of the tungsten lamp (typically 5 W);
power dissipation of the deuterium lamp (typically 25 to 30 W);
heat transfer of flow of heated sample or solvent (typically 0 to 20 W);
power dissipation of electronic circuitry, power supply and actuators.

The heat generated by the total power dissipation in the detector has to be transported to the outside. This can in principle be achieved by thermal conduction, thermal convection, thermal radiation, or forced air-cooling. In the prior art detector shown in FIG. 1, an arrangement 14 for forced air cooling, such as a fan, is employed for heat transfer. The arrows 15 indicate the direction of air flow. Air is thus transported by means of the fan 14 across the optical unit of the detector and then across the power supply and the electronic circuitry to the outside through openings in the detector housing.

The fan 14 also causes air to be drawn in through openings in the detector housing from the side opposite to the power supply and electronic circuitry (bottom of FIG. 1).

Under normal stationary conditions the power dissipation of electronic circuitry, lamps, actuators and power supply can be assumed to be constant and time invariant. The mentioned components are also only contributing to temperature effects on the measurement results to a smaller extent. Of greater concern are changes in the environmental conditions and the variation of the heat transfer of the sample or solvent as a consequence of a change of the analytical measuring parameters during the measurement.

Under normal operating conditions and with the assumption of constant ambient temperature the equilibrium is achieved after a certain amount of time, depending on the individual time constants of the various components. If, however, the ambient temperature is changing, all internal temperatures in the detector are changing according to the effective time constants given by thermal resistance and thermal capacitance. It can easily be shown, for example with the help of a model wherein the thermal conditions in the detector are expressed with electric circuit equivalents (heat as current, temperature as voltage, etc.), that ambient changes will modulate the internal temperatures. This causes thermal expansion, mechanical stress and therefore affects the optical properties of the system. The measuring signal is thus superimposed with temperature interaction effects so that the accuracy of the measuring results is impaired.

In the prior art, several attempts have been made to overcome the influence of ambient temperature changes. According to one approach, the forced air flow is varied by controlling the fan speed. In another approach, partial temperature control of specific functional blocks (optic or mechanic) is performed, for example by temperature stabilization of the optical unit, by using a flow heat exchanger, or by controlling the cooling air flow to the lamp housing. According to a third approach, it is attempted to keep the environmental conditions stable by employing air conditioning of the room in which the measuring instrument is located. In further prior art suggestions, sensitive functional blocks, for example the optical unit, are thermally insulated.

All the mentioned approaches provide only partial solutions to the problems associated with ambient temperature changes so that the effects of these changes on the measuring results cannot be suppressed or reduced to an acceptable level. Also, the prior art solutions are often technically complex and costly.

SUMMARY OF THE INVENTION

It is thus an object of the invention to provide a method of reducing the effects of varying environmental conditions on the measuring results in a measuring instrument which is comparatively simple to implement and which leads to a substantially reduced impairment of the measuring results by varying ambient temperature. It is also an object of the invention to provide a measuring instrument wherein the effects of varying ambient temperature on the measuring results are substantially reduced.

According to the invention, this object achieved by a method, with the measuring instrument comprising a measuring unit with components which are sensitive to varying environmental conditions, in that:

a) the measuring unit is thermally insulated such that the effects of variations in the environmental conditions on sensitive components are substantially reduced, but dissipated heat generated within the measuring unit can still leave the measuring unit; and b) the temperature in the measuring unit is controlled by means of a control loop comprising a temperature sensor and means to influence the temperature in the measuring unit in such a way that the temperatures at locations with sensitive components are kept substantially constant.

For a measuring instrument, the above mentioned object is achieved in that, a) a thermal insulation means is provided in the measuring instrument which substantially reduces the effects of variations in the environmental conditions on sensitive components, but still permits dissipated heat generated within the measuring unit to leave the measuring unit; and b) control means are provided for controlling the temperature in the measuring unit, wherein the control means comprise a temperature sensor and means to influence the temperature in the measuring unit in such a way that the temperatures at locations with sensitive components are kept substantially constant.

According to the invention, it has been realized that one of the reasons for the shortcomings of the prior art solutions is that they are only designed to achieve thermal stability at a specific location in the measuring unit so that other locations are still influenced by external ambient temperature variations. The present invention, however, provides for a temperature control so that the temperatures at all locations within the measuring unit are kept constant.

In a preferred embodiment of the invention a heater and a fan are used to direct an air stream of controlled temperature to the measuring unit. The heater is controlled with the help of a controller which receives as an input the output signal of a temperature sensor measuring the temperature of the air stream.

In a further development of this preferred embodiment, the target temperature for the temperature control, i.e. the input of the controller, is dynamically adapted to the actual ambient temperature conditions by using an additional temperature sensor for sensing ambient temperature. Preferably, the control range is in the order of the expected variation of the ambient temperature and the target temperature is above the ambient temperature. This has the advantage that only a heating and no cooling is required in the temperature control loop and that the power consumption is comparatively small.

When using the dynamic adaptation of the target temperature to the actual ambient temperature short term fluctuations (in the order of seconds) and medium term fluctuations (in the order of minutes) of the temperature can be fully compensated and long term fluctuations would only be noticeable as a long term drift which, however, is uncritical in typical measuring instruments, for example in optical detectors for liquid chromatography, since such a uniform drifting can easily be taken into account when processing the measuring results. On the other hand, the dynamic adaptation ensures a low power consumption and a comparatively simple technical design at low cost

In the following, embodiments of the invention will be described with reference to the drawings.

DETAILED DESCRIPTION OF THE INVENTION

Figure 2:
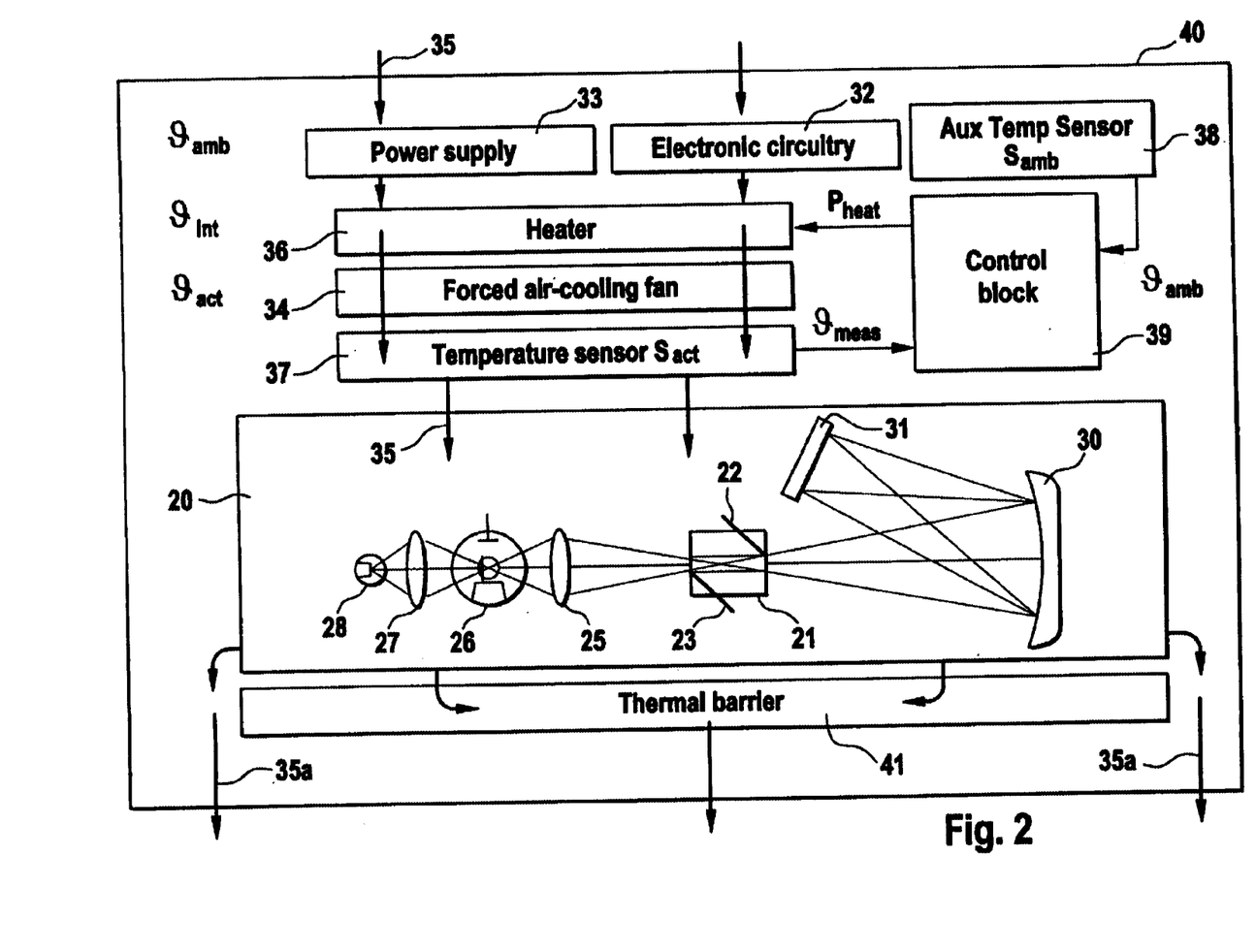
FIG. 2 is a block diagram of a detector for a liquid chromatograph according to an embodiment of the invention.

FIG. 2 is a block diagram of a liquid chromatography detector according to an embodiment of the invention. Block 20 comprises a flow cell 21 with inlet 23 and outlet 22 and optical components, such as tungsten lamp 28, deuterium lamp 26, lenses 27 and 25, diffraction grating 30 and photosensor 31, typically a photodiode array. The detector further comprises electronic circuitry 32, typically arranged on one or more printed circuit boards, and a power supply 33. The housing of the detector is schematically indicated with reference numeral 40.

A fan 34 for forced air-cooling is arranged inside the detector between block 20 and power supply 33 and electronic circuitry 32. The fan 34 generates an air flow as indicated by the arrows 35 towards block 20. A heater 36 is arranged in the air flow at one side of the fan 34. At the other side of the fan 34, a temperature sensor 37 is located. The output signal ($\vartheta_{meas}$) of the temperature sensor 37 is supplied to a temperature control block 39. An auxiliary temperature sensor 38 is located near the rear end of the detector housing for monitoring the ambient temperature. The output signal ($\vartheta_{amb}$) of the auxiliary temperature sensor is supplied to the temperature control block 39. The temperature control block 39 generates a power signal (P heat) to control the heater 36 using an algorithm which will be explained in more detail below. The control block 39 is implemented in firmware, but it could also be realized either in software or with discrete analog or digital circuitry.

At the front side of the detector, a thermal barrier 41 is arranged for preventing heat transfer from the outside against the direction of air flow. The thermal barrier 41 in an embodiment of the invention is made of foamed material and has a typical thickness of a few millimeters. The thermal barrier could also be made of other materials or be realized by constructive design. The thermal barrier 41 and the chosen direction of air flow prevent that variations of ambient parameters (temperature, humidity, air velocity, etc.) can directly reach the sensitive components of the detector in block 20. In order to prevent that the heat generated in block 20, for example by the lamps, heats up the detector, small openings are provided at the front side through which excess heat can escape to the outside. This is illustrated in FIG. 2 in that the arrows 35 for the air flow extend into the thermal barrier 41 and from there to the outside. Alternatively, small openings may be provided at the periphery of the thermal barrier through which the heated air is transported to the outside (arrows 35a). The openings are sufficiently small so that changes of the ambient conditions do not directly reach the sensitive components of the detector.

Figure 3:
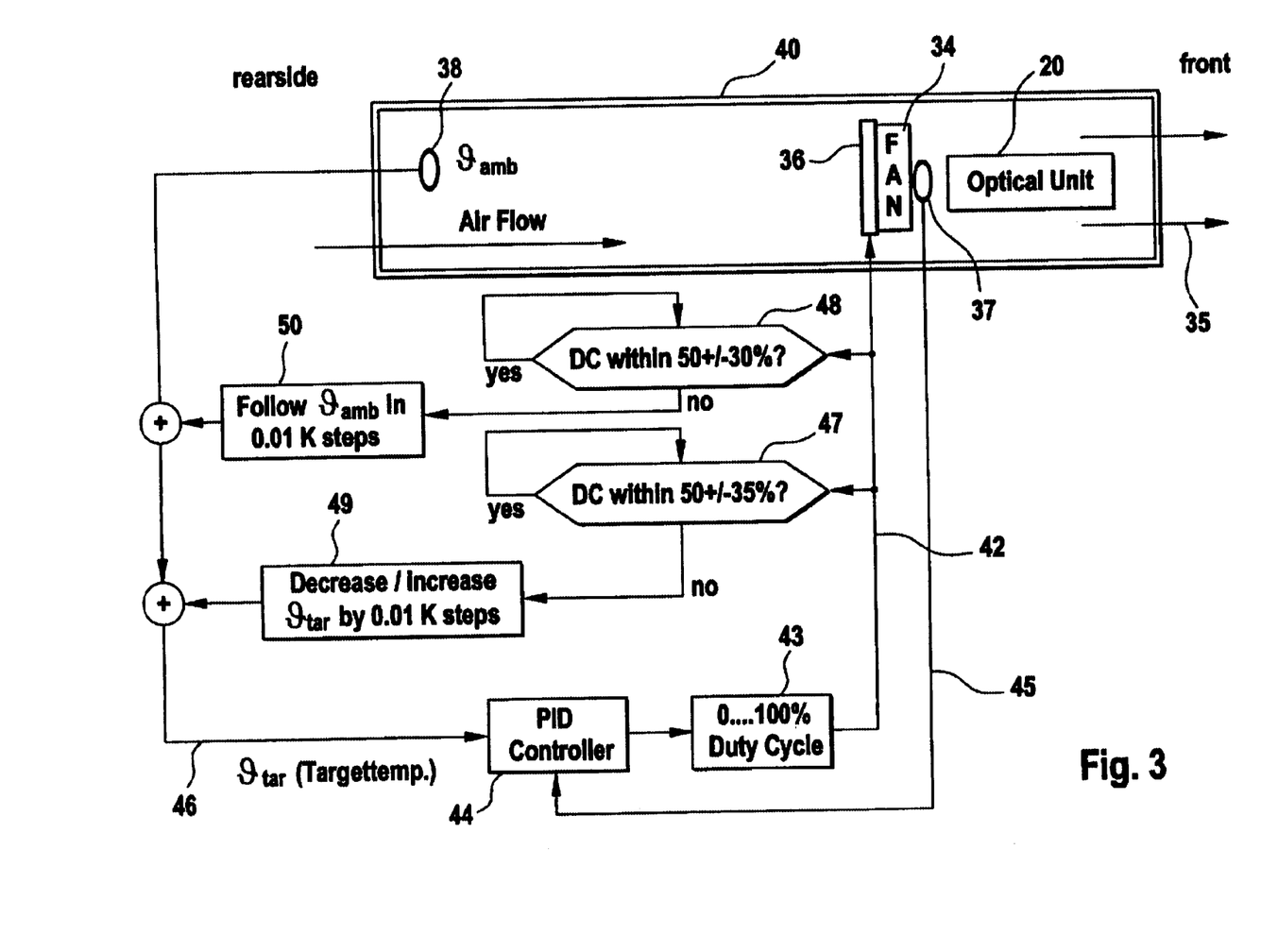
FIG. 3 illustrates the principle of operation of the embodiment of the invention shown in FIG. 2 with the help of a flow diagram.

In the following, the control algorithm used in the detector shown in FIG. 2 will be explained in detail. Reference is made to FIG. 3 which illustrates the principle of operation with the help of a flow diagram. FIG. 3 also depicts in a schematic way the detector housing 40, the optical unit 20 arranged inside the detector, the fan 34 for forced air cooling, the heater 36, the temperature sensor 37, and the auxiliary temperature sensor 38 for sensing ambient temperature. The direction of air flow is indicated with arrows 35.

The heating power of the heater 36 is controlled by an input signal supplied on line 42. In the present example, the heating power is determined by the duty cycle of the signal on line 42. The appropriate duty cycle is determined by a PID controller 44 in response to input signals on lines 45 and 46. The input signal on line 45 corresponds to the temperature measured by the sensor 37 between fan 34 and optical unit 20, and the input signal online 46 corresponds to the target temperature the significance of which will be explained later. A signal generation circuit 43 produces the output signal for the heater 36 having the thus determined duty cycle.

A circuit 48 determines whether the duty cycle (DC) of the signal on the line 42 lies within a first predefined range. In the present example, this range has been chosen as 50% +/−30% duty cycle, that means between 20% and 80% duty cycle. If the duty cycle is within that range, no further steps are taken. If the duty cycle is outside of that range, a control signal is generated which causes a circuit 50 to influence the signal on line 46 such that it follows the ambient temperature in small steps, such as steps of 0,01 degrees Kelvin.

A circuit 47 determines whether the duty cycle (DC) of the signal on the line 42 lies within a second predefined range. The second predefined range typically encompasses the first predefined range. In the present example, the second predefined range has been chosen as 50% +/−35% duty cycle, that means between 15% and 85% duty cycle. If the duty cycle lies within that range, no further steps are taken. If the duty cycle is outside of that range, a control signal is generated which causes a circuit 49 to influence the signal on line 46 such that it represents a higher or lower target temperature. In the present example, the target temperature is thus increased or decreased in steps of 0,01 degrees Kelvin.

The following of the ambient temperature with circuit 50 occurs at a slower rate than the stepwise decrease or increase of the target temperature with circuit 49. In a practical example, changes at the output of block 50 representing a temperature change occur each 8 seconds, whereas corresponding changes at the output of block 49 may occur each 2 seconds. Block 49 thus serves for an accelerated target temperature adjustment and helps to bring the duty cycle quickly back into its normal operating range.

If, after corresponding increase or decrease of the temperature signals from blocks 49 and 50, the duty cycle has returned to its normal range (20% to 80% in the example), the target temperature supplied to the controller 44 at this time is used as the new nominal value for the control of the heater 36. The control range for temperature regulation is in the order of the expected ambient temperature variation and the target is set to the middle of the control range (50% duty cycle) at the end of the warm-up phase.

The conditions during warm-up will be described in the following. Since the temperature regulator is designed substantially for an operating range in the order of somewhat above the expected ambient variation for suppressing ambient variations instead of an overall temperature stabilization, the target point for temperature setting has to be determined. During an initial time interval after switching on the instrument or after changing the lamp status, the control is switched off and the duty cycle on line 42 is set to 50%. During this interval the temperature of the sensor 37 at the fan 34 is monitored and at the end of this interval a weighted average of the measured temperatures is calculated and used as input ("target temperature") for the controlled operation mode. In a second time interval, typically of similar duration as the first interval (e.g. 30 minutes), the control is switched on and set to "fast response". Fast response means that the increase or decrease of the temperature signals from blocks 49 and 50 is performed faster than described above in connection with the normal operation of the control circuits. The corresponding speed of change may increase, for example, by a factor of 5 to 10. After this second time interval, normal control operation starts as described above.

Figure 4:
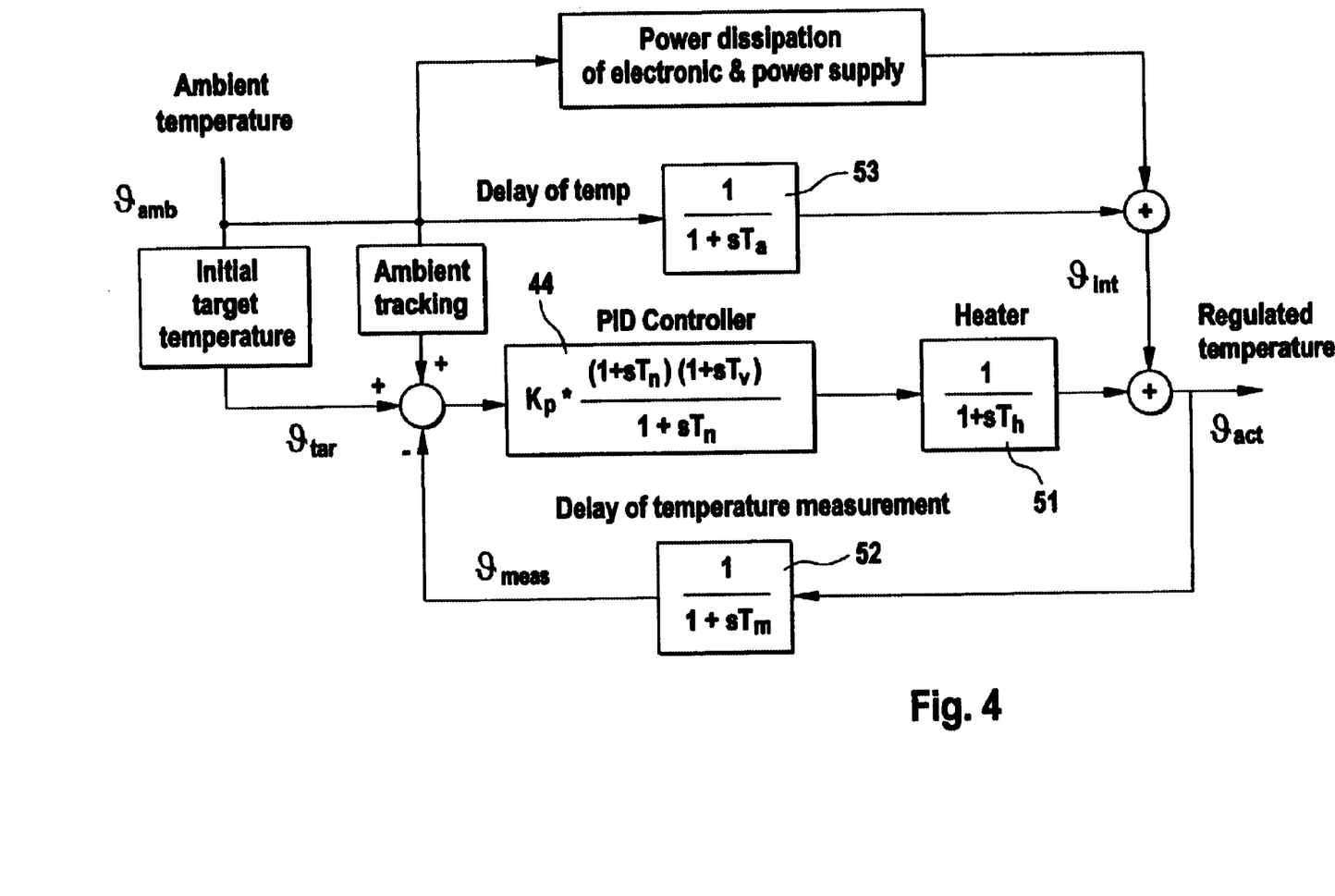
FIG. 4 is a block diagram of the temperature control loop, further explaining the embodiment according to FIGS. 2 and 3.

The operation of the temperature control loop of the embodiment described above in connection with FIGS. 2 and 3 will now be explained further with reference to FIG. 4. FIG. 4 is a block diagram using Laplace nomenclature. $T_h$, $T_m$ and $T_a$ represent the time constants of the delays of the heater response (block 51), of the delay of the temperature measurement with the temperature sensor (block 52), and of the delay of the air temperature change from ambient to heater location (block 53), respectively. The parameter $K_p$ represents the gain factor of the PID controller 44 and $T_n$, $T_v$ are parameters to describe the time response of the controller.

The behavior of the temperature control loop can be optimized with respect to response of target temperature and/or ambient temperature change by carefully determining the parameters of the PID regulator $K_p$, $T_n$, $T_v$. In the following paragraphs the transfer characteristic of changes with regard to target temperature and ambient changes are described and the regulator parameters $K_p$, $T_n$, $T_v$ for best behavior are determined.

a) Description of Target Transfer Function and Determination of the Controller Parameter.

The closed loop transfer function regarding the target temperature of the temperature control loop given above is:

$$F(s) = \frac{Kp \cdot \frac{(1+sTn) \cdot (1+sTv)}{sTn \cdot (1+sTh)}}{1 + Kp \cdot \frac{(1+sTn) \cdot (1+sTv)}{sTn \cdot (1+sTh) \cdot (1+sTm)}} \quad (1)$$

With the assumption that: $T_v = T_m$ and $T_n = T_h$ the equation (1) simplifies to:

$$F(s) = Kp \cdot \frac{1+sTv}{Kp+sTn} = \frac{1+sTm}{1+s\frac{Th}{Kp}} \quad (2)$$

From the equation (2) the parameter for gain $K_p$ can now be derived. With $T_m = T_h/K_p$ for fastest response the value for gain of the controller is determined to be:

$$K_p = T_h/T_m \quad (3)$$

b) Description of the Transfer Function of Ambient Temperature Changes:

According to the model of the temperature control loop as shown in FIG. 4 the response to ambient changes can be described as:

$$\vartheta_{act} = \vartheta_{amb} \cdot \left(\frac{1}{1+sTa}\right) + \left(\vartheta_{target} - \frac{\vartheta_{act}}{1+sTm}\right) \cdot Kp \cdot \frac{(1+sTn) \cdot (1+sTv)}{sTn \cdot (1+sTh)} \quad (4)$$

With $T_v = T_m$ and $T_n = T_h$ the equation (4) is simplified to:

$$\vartheta_{act}(s) = \frac{\vartheta_{amb} \cdot sTn}{(1+sTa) \cdot (Kp+sTm)} + \vartheta_{var} \cdot Kp(1+sTm) \cdot \frac{sTm}{(Kp+sTm) \cdot Tm} \quad (5)$$

It should be noted that only the first term depends on ambient temperature. The response of the actual internal temperature $\vartheta_{act}$ to ambient temperature variation is determined by:

$$F_{amb}(s) = \frac{\Delta\vartheta_{act}(s)}{\Delta\vartheta_{amb}(s)} = \frac{sTm}{Kp \cdot (1+sTa) \cdot \left(1+s\frac{Tm}{Kp}\right)} \quad (6)$$

Equation (7) describes the step response of $\vartheta_{act}$ expressed in s-domain.

$$\vartheta_{act}(s) = \frac{1}{s} \cdot F_{amb}(s) = \frac{Th}{Kp} \cdot \frac{1}{(1+sTa) \cdot \left(1+s\frac{Tm}{Kp}\right)} \quad (7)$$

Back transformation into the time domain gives:

$$\vartheta_{act}(t) = \frac{Th}{Kp} \cdot \frac{e^{-\frac{t}{Ta}} - e^{-\frac{t \cdot Kp}{Tm}}}{Ta - \frac{Tm}{Kp}} \quad (8)$$

Figure 5:
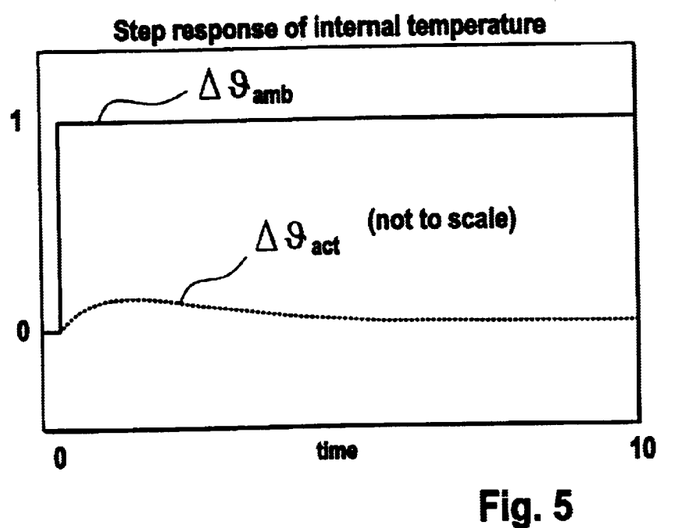
FIG. 5 is a graphical representation of temperature as a function time, illustrating the response of the internal temperature to an abrupt change of the ambient temperature, according to an example of the invention.

The result of equation (8), which describes the response of $\vartheta_{act}$ to a step of $\vartheta_{amb}$ is shown in FIG. 5.

As an alternative to the control method described in connection with FIG. 3, it would also be possible to use only one temperature sensor, since the actual duty cycle of the heater power signal on line 42 represents the deviation of the ambient temperature relative to the target temperature. On the other hand, an additional sensor like the auxiliary temperature sensor 38 can be used to get information about the rate of temperature change. With this information the algorithm for temperature regulation can be optimized. As a further alternative to the method described in connection with FIG. 3, one could define more control ranges than just the three ranges in this embodiment, i.e., range between 20 and 80% duty cycle, range 15–20% and 80–85% duty cycle, range 0–15% and 85–100% duty cycle. Like in the described embodiment, the adjustment increments (target temperature increments) associated with a specific control range would in such an alternative embodiment increase with the deviation from the midpoint (50% duty cycle). Another possibility is a continuous increase of adjustment increments depending on the deviation from the midpoint.

Figure 7A:
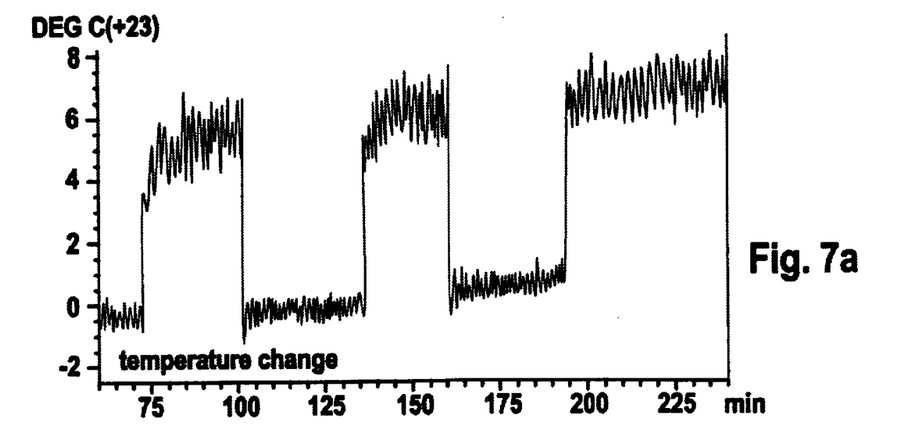
FIGS. 7a–7c show three measuring curves illustrating the improvement over the prior art achieved with the invention.
Figure 7B:
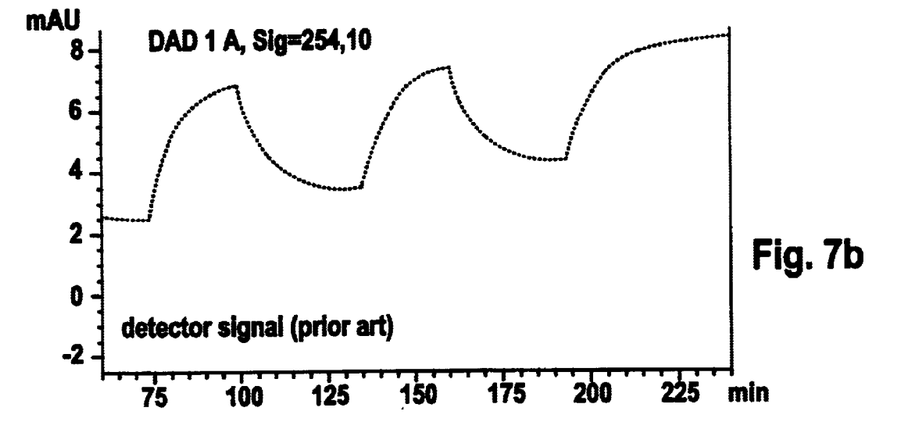
Figure 7C:
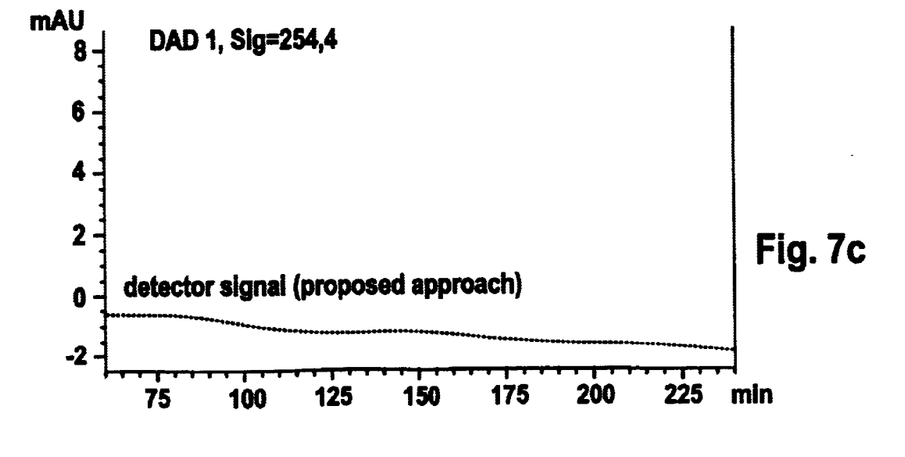

FIGS. 7a–7c illustrate the improvement achieved with the present invention over the prior art with the example of three actual measuring curves. The measuring curves were recorded with a liquid chromatography detector of the type shown in FIG. 1 and FIG. 2, i.e. a liquid chromatography absorbance detector with a photodiode array.

FIG. 7a shows a time variation of the ambient temperature which has been generated for measurement purposes. The vertical axis of the graphical representation is the deviation of the ambient temperature (in degrees centigrade) from a normal ambient temperature value, and the horizontal axis is the elapsed time (in minutes).

FIG. 7b shows the detector signal of a prior art detector which was subject to the ambient temperature changes represented in FIG. 7a. The vertical axis represents the absorption signal of the detector in milli absorbance units (mAU), and the horizontal axis is the elapsed time. The measurement according to FIG. 7b was made without sample substances flowing through the detector flow cell, so that the variation in the detector signal is solely due to the ambient temperature changes. It can be seen that the temperature changes produce peaks in the detector signal synchronously with the temperature variation. If real sample substances are measured, these temperature induced peaks would interfere with the sample peaks and thus substantially impair the measuring accuracy.

FIG. 7c shows the detector signal of a detector in accordance with the present invention which is subject to the same ambient temperature variations as the prior art detector of FIG. 7b. It can be seen that the signal is substantially smooth and, in contrast to the prior art, has no artificial peaks which could interfere with the sample peaks.

In the following, a further development of the invention will be described which is particularly useful for detectors wherein the liquid being analyzed in the detector may transport heat into the detection system. In many liquid chromatography applications, for example, the eluent (solvent) and the separation column are heated in an oven in order to optimize the separation process of the compounds. Heat can thus be transferred into the detection system by the solvent passing through the flow cell. The amount and the direction of transferred heat depends on the solvent temperature, the flow rate, the temperature of the flow cell environment, and the thermal properties of the solvent which in turn is a dependent on the solvent composition. Specifically, the transferred amount of heat is the product of the flow rate, time, temperature difference between flow cell inlet and outlet, the specific heat of the liquid in the flow cell and its mass density.

The factors which determine the amount of transferred heat, such as flow rate, solvent temperature, solvent composition are often varied during a chromatographic analysis in order to optimize the separation. Due to these variations, the amount of heat transferred to the measurement system can vary significantly. As a consequence thereof, the thermal equilibrium is disturbed causing drift on the measuring signal and inaccuracies of the measuring results.

In the prior art there are two approaches to prevent heat transfer from the solvent to the measuring system. According to the first approach, a passive heat exchanger is provided to approximate the solvent temperature to the operating temperature at the position of the flow cell. In the second approach, the flow cell is thermally insulated to avoid heat transfer into the system. Both approaches have disadvantages. First, a passive heat exchanger approximates the temperature to a level which may differ from the required cell environmental temperature so that the result may not be satisfactory. Second, in case of thermal insulation of the flow cell, the temperature of the solvent passing through the cell still depends on the analytical parameter and may affect the characteristics of the optical path by refractive index changes.

In accordance with a further development of the present invention, heat transfer from the solvent is avoided by equalizing the solvent inlet temperature with the temperature of the flow cell environment. Since the temperature of the cell environment depends on the target temperature of the temperature regulator, a two-stage flow heat exchanger is used.

The first stage is a passive heat sink with fins which is placed in air flow. It uses the thermal capacitance to reduce the temperature difference between heated solvent and flow cell environment and damps variations in heat transfer caused by variations in flow rate, solvent temperature and solvent composition.

Figure 6:
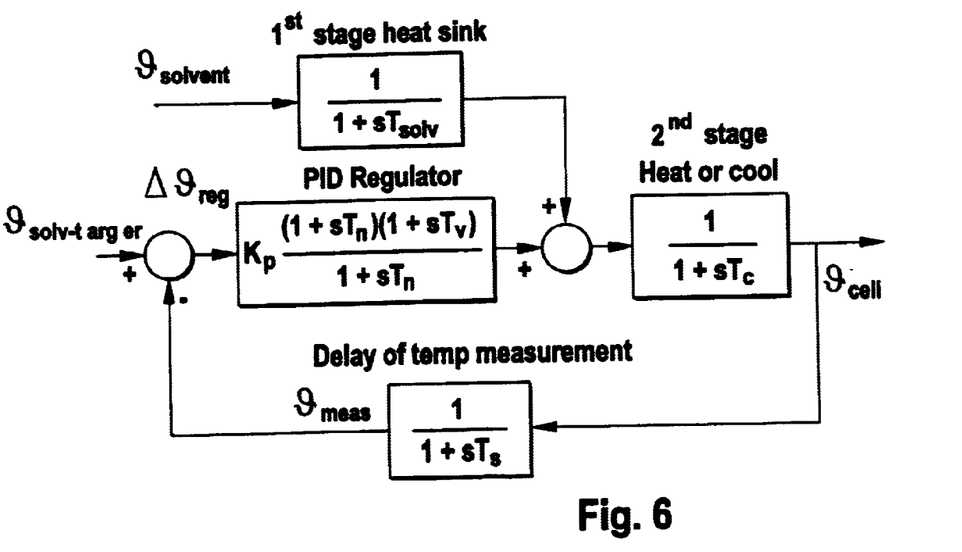
FIG. 6 illustrates the temperature control loop used for avoiding heat transfer from the detector sample cell according to a further development of the invention.

The second stage is an actively controlled heat exchanger with means for heating and/or cooling, e.g. a Peltier element, with associated temperature controller. It is also possible to combine both stages, but the best results are achieved with two separated stages in series, especially if the second stage is thermally isolated from the first stage. The temperature control loop for such a two-stage flow heat exchanger is schematically illustrated in FIG. 6. Tc denotes the time constant of the delay of the second stage heater/cooler; Ts denotes the time constant of the delay of the temperature measurement with the temperature sensor. Tsolv represents the time constant of the passive first stage heat sink. Kp and, Tn and Tv are parameters of the PID regulator. The values of these parameters are determined in a similar way as determined for ambient temperature regulation. The letter denotes various temperatures as specifically indicated by the subscripts. The subscript "solvent" refers to solvent temperature, "cell" to sample cell temperature, "meas" to measured temperature, "solv-target" to the desired solvent temperature.

Various modifications to the above described embodiments of the invention are possible, depending on specific requirements and desired applications. In the embodiment shown in FIG. 2 the fan with the heater and temperature sensor are placed in the middle of the instrument and the cooling air flows first through the electronic circuitry and the power supply before it is temperature stabilized. Then the air flow passes the optical unit and exits through the front side. This is advantageous in cases where the characteristics of the electronic circuitry and the power supply are not particularly sensitive to ambient temperature changes or if the power dissipation of these functional blocks is not varying with time. In both cases the thermal time constants of these blocks act as additional thermal low pass and the temperature regulation results in better performance.

If other components with variable power dissipation are present in the system, then local control of heat transfer may be advantageous, similar to the above described flow cell heat exchanger. The precise direction of air flow is only of secondary importance. It is, however, important that the temperature stabilization unit is located in front of or close to the temperature sensitive functional blocks of the instruments. Furthermore, there should be no bypasses at temperature sensitive functional blocks with unregulated air flow.

What is claimed is:

1. A method of reducing effects of varying environmental conditions on a measuring instrument having a measuring unit, said method comprising:

thermally insulating said measuring unit such that effects of varying environmental conditions on selected components of said measuring unit are substantially reduced, while allowing dissipated heat generated within said measuring unit to leave said measuring unit; and controlling a first temperature in said measuring unit by means of a control loop having a temperature sensor and means to influence said first temperature in said measuring unit in such a way that temperatures at locations with selected components are kept substantially constant, wherein said first temperature in said measuring unit is related to an ambient temperature, and wherein said first temperature is controlled within a range of an order of an expected variation of said ambient temperature.

2. The method of claim 1, wherein said step of thermally insulating comprises arranging a thermal barrier between said measuring unit and a housing of said measuring instrument.

3. The method of as in claim 1, wherein said first temperature in said measuring unit is above said ambient temperature.

4. The method of claim 1, wherein said measuring instrument includes a liquid chromatography detector.

5. The method of claim 1, wherein said first temperature is above said ambient temperature by about one half of said expected variation of said ambient temperature.

6. The method of claim 1, wherein said measuring instrument comprises a liquid chromatography absorbance detector.

7. A method of reducing effects of varying environmental conditions on a measuring instrument having a measuring unit, said method comprising:

thermally insulating said measuring unit such that effects of varying environmental conditions on selected components of said measuring unit are substantially reduced, while allowing dissipated heat generated within said measuring unit to leave said measuring unit; and controlling a first temperature in said measuring unit by means of a control loop having a temperature sensor and means to influence said first temperature in said measuring unit in such a way that temperatures at locations with selected components are kept substantially constant, wherein said step of controlling a first temperature includes:

directing air to said measuring unit utilizing a fan;

heating said air directed to said measuring unit; and measuring the temperature of said heated air and using said measured temperature as an input signal to said control loop.

8. The method of claim 7, comprising the additional steps of:

measuring a temperature ($\eta_{amb}$) close to said housing where ambient air enters said measuring instrument; and deriving from said temperature ($\eta_{amb}$) an additional input signal to said control loop.

9. A measuring instrument that includes a measuring unit having components that are sensitive to varying environmental conditions, said measuring instrument comprising:

thermal insulation arranged in said measuring instrument so as to substantially the reduce effects of said varying environmental conditions on selected components, and to permit dissipated heat generated within said measuring unit to leave said measuring unit; and a controller for controlling a first temperature in said measuring unit, said controller having:
a temperature sensor; and
means to influence said first temperature in such a way that temperatures at locations of said selected components are kept substantially constant,
wherein said first temperature in said measuring unit is related to an ambient temperature, and
wherein said first temperature is controlled within a range of an order of an expected variation of said ambient temperature.

10. The measuring instrument of claim 9, wherein said thermal insulation comprises a thermal barrier arranged between said measuring unit and a housing of said measuring instrument.

11. The measuring instrument of claim 9, wherein said measuring instrument comprises an optical detector.

12. A measuring instrument that includes a measuring unit having components that are sensitive to varying environmental conditions, said measuring instrument comprising:

thermal insulation arranged in said measuring instrument so as to substantially reduce effects of said varying environmental conditions on selected components, and to permit dissipated heat generated within said measuring unit to leave said measuring unit; and a controller for controlling a first temperature in said measuring unit, said controller having:
a temperature sensor;
means to influence said first temperature in such a way that temperatures at locations with said selected components are kept substantially constant;
a fan for directing air to said measuring unit;
a heater for heating said directed air;
a temperature sensor for measuring a temperature of said heated air; and
a control loop connected to said temperature sensor and to said heater.

13. The measuring instrument of as in claim 12, further comprising an additional temperature sensor located in close proximity to said housing where ambient air enters said measuring instrument, wherein said additional temperature sensor provides an additional input signal to said control loop.

14. A measuring instrument that includes a measuring unit having components that are sensitive to varying environmental conditions, said measuring instrument comprising:

thermal insulation arranged in said measuring instrument so as to substantially reduce effects of said varying environmental conditions on selected components, and to permit dissipated heat generated within said measuring unit to leave said measuring unit; and a controller for controlling a first temperature in said measuring unit, said controller having:
a temperature sensor; and
means to influence said first temperature in such a way that temperatures at locations with said selected components are kept substantially constant,
wherein said measuring unit includes:
a flow cell through which solvent can flow; and
additional means for adapting a solvent inlet temperature of an environment of said flow cell.

* * * * *